United States Patent
Olson (10) Patent No.: US 9,820,677 B2
(45) Date of Patent: Nov. 21, 2017

(54) COINTEGRATION FILTER FOR A CATHETER NAVIGATION SYSTEM

(71) Applicant: St. Jude Medical, Atrial Fibrillation Division, Inc., St. Paul, MN (US)

(72) Inventor: Eric S. Olson, Maplewood, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 785 days.

(21) Appl. No.: 13/733,521

(22) Filed: Jan. 3, 2013

(65) Prior Publication Data

US 2014/0187905 A1 Jul. 3, 2014

(51) Int. Cl.
*A61B 5/05* (2006.01)
*A61B 5/06* (2006.01)
(Continued)

(52) U.S. Cl.
CPC .............. *A61B 5/066* (2013.01); *A61B 5/042* (2013.01); *A61B 5/0538* (2013.01); *A61B 5/062* (2013.01); *A61B 5/068* (2013.01); *A61B 5/72* (2013.01); *A61B 5/743* (2013.01); *A61B 5/7425* (2013.01); *A61B 8/0883* (2013.01); *A61B 8/12* (2013.01); *A61B 17/00234* (2013.01);
(Continued)

(58) Field of Classification Search
None
See application file for complete search history.

(56) References Cited

U.S. PATENT DOCUMENTS 6,063,022 A * 5/2000 Ben-Haim ............... 600/41
6,288,785 B1 * 9/2001 Frantz ................. A61B 5/06
250/559.29

(Continued)

FOREIGN PATENT DOCUMENTS

EP 2168478 3/2010
EP 2465430 6/2012
(Continued)

OTHER PUBLICATIONS

Murray, Michael P., "A Drunk and Her Dog: An Illustration of Cointegration and Error Correction," 48 The American Statistician No. 1 pp. 37-39 (1994).
(Continued)

*Primary Examiner* — James Kish
(74) *Attorney, Agent, or Firm* — Dykema Gossett PLLC (57) ABSTRACT

A system and method for determining a position of a medical device within a body are provided. The system includes an electronic control unit that receives position signals from position sensors of a first type and a second type disposed on the device and applies a filter to each of the position signals to obtain filtered estimated positions for each sensor. The unit computes a spline connecting the position sensors of the first type responsive to the filtered estimated positions for the sensors and estimates a spline position for the sensor of the second type along the spline. The unit generates maps between the spline position and filtered and unfiltered estimated positions for the sensor of the second type and determines actual positions for the sensors of the first type responsive to the filtered estimated position for the sensors and a composite map of the two maps.

18 Claims, 3 Drawing Sheets

(51) Int. Cl.

| | |
|---|---|
| A61B 17/00 | (2006.01) |
| A61B 18/02 | (2006.01) |
| A61B 18/18 | (2006.01) |
| A61B 5/042 | (2006.01) |
| A61B 5/053 | (2006.01) |
| A61B 5/00 | (2006.01) |
| A61B 8/08 | (2006.01) |
| A61B 8/12 | (2006.01) |
| A61M 25/01 | (2006.01) |
| A61M 25/09 | (2006.01) |
| A61M 5/142 | (2006.01) |
| A61M 5/178 | (2006.01) |
| A61N 7/02 | (2006.01) |
| A61B 34/20 | (2016.01) |

(52) U.S. Cl.
CPC .............. *A61B 18/02* (2013.01); *A61B 18/18* (2013.01); *A61B 34/20* (2016.02); *A61M 5/142* (2013.01); *A61M 5/178* (2013.01); *A61M 25/0105* (2013.01); *A61M 25/09* (2013.01); *A61N 7/022* (2013.01); *A61B 5/063* (2013.01); *A61B 2034/2051* (2016.02); *A61B 2034/2053* (2016.02)

(56) References Cited

U.S. PATENT DOCUMENTS

| | | | |
|---|---|---|---|
| 7,263,397 B2 | 8/2007 | Hauck et al. | |
| 7,386,339 B2 | 6/2008 | Strommer et al. | |
| 2006/0039623 A1* | 2/2006 | Chaudhury | G06T 3/403 |
| | | | 382/266 |
| 2008/0161681 A1 | 7/2008 | Hauck | |
| 2009/0103793 A1* | 4/2009 | Borland et al. | 382/131 |
| 2009/0247942 A1 | 10/2009 | Kirschenman | |
| 2009/0247944 A1 | 10/2009 | Kirschenman et al. | |
| 2009/0247993 A1 | 10/2009 | Kirschenman et al. | |
| 2009/0248042 A1 | 10/2009 | Kirschenman | |
| 2010/0152571 A1* | 6/2010 | Hartmann et al. | 600/424 |
| 2010/0256558 A1 | 10/2010 | Olson et al. | |
| 2011/0015569 A1 | 1/2011 | Kirschenman et al. | |
| 2011/0029278 A1* | 2/2011 | Tanigawa | G01S 5/0294 |
| | | | 702/150 |
| 2011/0091088 A1* | 4/2011 | Wilson et al. | 382/131 |
| 2012/0157825 A1 | 6/2012 | Koyrakh et al. | |
| 2012/0302869 A1 | 11/2012 | Koyrakh et al. | |

FOREIGN PATENT DOCUMENTS

| | | |
|---|---|---|
| EP | 2471482 | 7/2012 |
| WO | WO2009/120982 | 10/2009 |
| WO | WO 2009/128062 | 7/2012 |

OTHER PUBLICATIONS

International Search Report and Written Opinion issued in International (PCT) Patent Application No. PCT/US2013/075652 (dated Mar. 19, 2014).

\* cited by examiner

COINTEGRATION FILTER FOR A CATHETER NAVIGATION SYSTEM

BACKGROUND a. Field

This disclosure relates to a system and method for determining a position of a medical device within a body. In particular, the instant disclosure relates to a system and method that use a beneficial characteristic of one type of position sensor on the medical device to improve the accuracy of position information provided by another type of position sensor on the device.

b. Background Art

A wide variety of medical devices are inserted into the body to diagnose and treat various medical conditions. Catheters, for example, are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is used to puncture the skin surface and a sheath having an inner diameter greater than the outer diameter of the catheter is threaded through the vasculature to a region of interest. The catheter is then moved longitudinally through the sheath to the region of interest either manually by a clinician or through the use of electromechanical drive systems.

It is desirable to track the position of medical devices such as catheters as they are moved within the body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and physician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a physician through, for example, a visual display.

One type of medical device navigation system is made available under the trademark "ENSITE NAVX" by St. Jude Medical, Inc. The system is based on the principle that when electrical currents are passed through the thorax a voltage drop occurs across internal organs such as the heart and this voltage drop can be measured and used to determine the position of a medical device within the body. The system includes three pairs of patch electrodes that are placed on opposed surfaces of the body (e.g., chest and back, left and right sides of the thorax, and neck and leg) and form generally orthogonal x, y, and z axes as well as a reference electrode that is typically placed near the stomach and provides a reference value and acts as the origin of the coordinate system for the navigation system. Sinusoidal currents are driven through each pair of patch electrodes and voltage measurements for one or more electrodes or other electrical position sensors associated with the medical device are obtained. The measured voltages are proportional to the distance of the electrical position sensors from the patch electrodes. The measured voltages are compared to the potential at the reference electrode and the position of the electrical position sensors within the coordinate system of the navigation system is determined. This system can be used to provide a substantially accurate indication of the position of the medical device within a body. The voltage measurements generated by the electrical position sensors, however, may suffer from undesirable levels of noise thereby impairing accuracy. Further, filtering of the noise may cause delays in generating position information.

Another type of medical device navigation system is made available under the trademark "MEDIGUIDE" by St. Jude Medical, Inc. The system is based on the principle that time varying magnetic fields may be used to induce a current on a magnetic position sensor such as a coil on a medical device within the body that can be used to determine the position of the medical device within the body. The signals generated by the magnetic position sensors generally suffer from less noise than the signals generated by the electrical position sensors in the electric field based system. Magnetic positions sensors, however, are generally more expensive and more difficult to place on a medical device thereby limiting the number of sensors that may be used.

BRIEF SUMMARY

The present disclosure relates to a system and method for determining a position of a medical device within a body. In particular, the present disclosure relates to a system and method that use a beneficial characteristic of one type of position sensor on the medical device to improve the accuracy of position information provided by another type of position sensor on the device.

A system for determining a position of a medical device within a body includes an electronic control unit configured to receive a position signal from each of a plurality of position sensors of a first type disposed on the medical device and from at least one position sensor of a second type disposed on the medical device. The electronic control unit is further configured to apply a filter to each of the position signals to obtain filtered estimated positions for each of the plurality of position sensors of the first type and the at least one position sensor of the second type. The electronic control unit is further configured to compute a spline connecting the plurality of position sensors of the first type responsive to the filtered estimated positions for the plurality of positions sensors of the first type and to estimate a spline position for the at least one position sensor of the second type along the spline. The electronic control unit is further configured to generate a first map between the spline position and the filtered estimated position of the at least one position sensor of the second type and to generate a second map between the spline position and an unfiltered estimated position of the at least one position sensor of the second type. The electronic control unit is further configured to generate a composite map responsive to the first and second maps and to determine an actual position for one of the plurality of position sensors of the first type responsive to the composite map and the filtered estimated position for the one position sensor of the first type.

A method for determining a position of a medical device within a body includes receiving a position signal from each of a plurality of position sensors of a first type disposed on the medical device and from at least one position sensor of a second type disposed on the medical device. The method further includes applying a filter to each of the position signals to obtain filtered estimated positions for each of the plurality of position sensors of the first type and the at least one position sensor of the second type. The method further includes computing a spline connecting the plurality of position sensors of the first type responsive to the filtered estimated positions for the plurality of positions sensors of the first type and estimating a spline position for the at least one position sensor of the second type along the spline. The method further includes generating a first map between the spline position and the filtered estimated position of the at least one position sensor of the second type and generating a second map between the spline position and an unfiltered estimated position of the at least one position sensor of the second type. The method further includes generating a composite map responsive to the first and second maps and determining an actual position for one of the plurality of position sensors of the first type responsive to the composite map and the filtered estimated position for the one position sensor of the first type.

The disclosed system and method make use a beneficial characteristic of one type of position sensor on the medical device to improve the accuracy of position information provided by another type of position sensor on the device. In one embodiment, for example, the position information generated by one or more magnetic position sensors—which are characterized by relatively low noise—may be used to improve the accuracy of positional information generated by lower cost electrical position sensors.

The foregoing and other aspects, features, details, utilities, and advantages of the present invention will be apparent from reading the following description and claims, and from reviewing the accompanying drawings.

DETAILED DESCRIPTION

Figure 1:
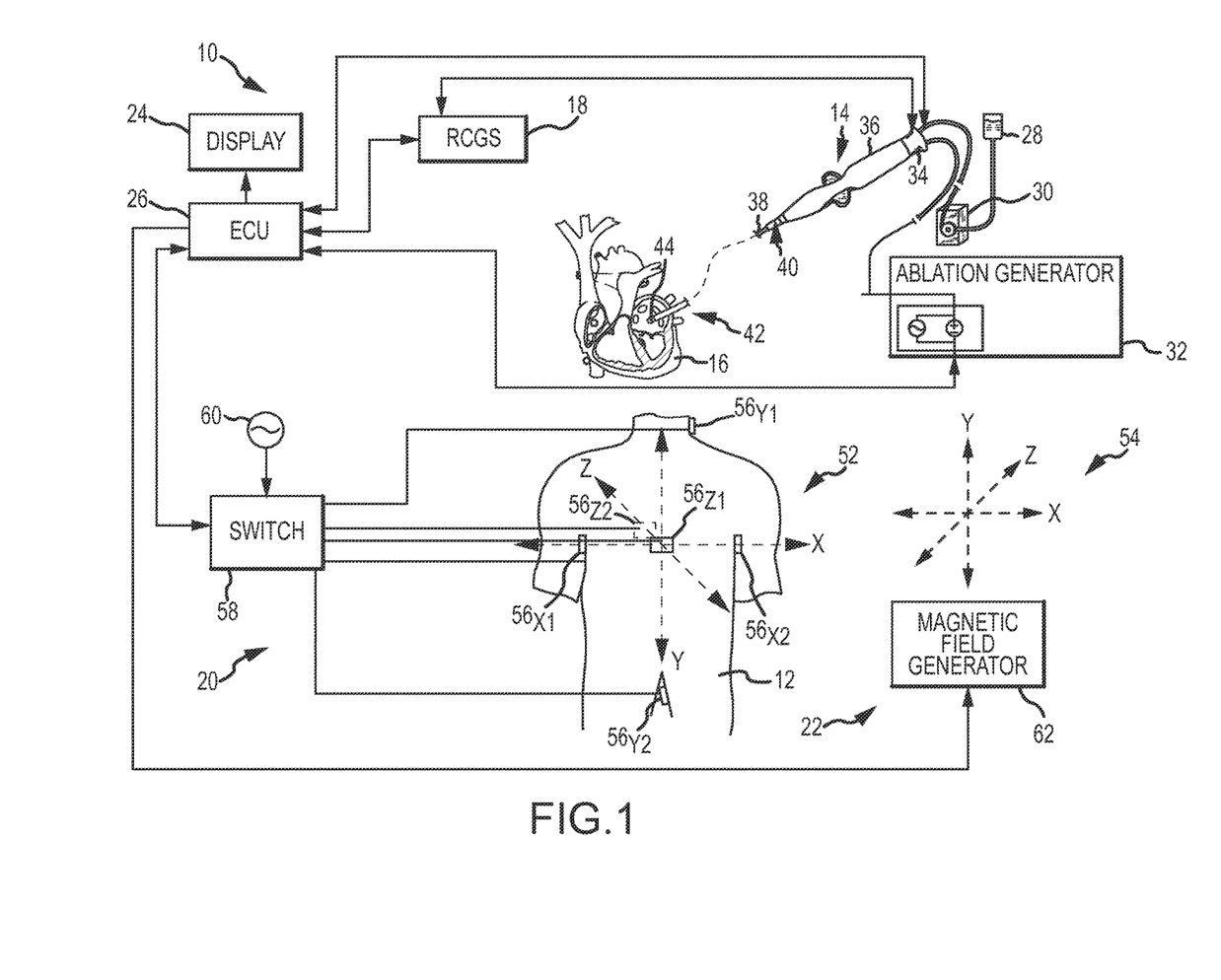
FIG. 1 is diagrammatic view of one embodiment of a system for determining a position of a medical device within a body in accordance with the present teachings.

Referring now to the drawings wherein like reference numerals are used to identify identical components in the various views, FIG. 1 illustrates one embodiment of a system 10 for determining a position of a medical device within a body 12. In the illustrated embodiment, the medical device comprises a catheter 14 and, in particular, an irrigated ablation catheter for use in diagnosis or treatment of cardiac tissue 16 in body 12. It should be understood, however, that a system 10 in accordance with the present teachings may find application in connection with a wide variety of medical devices used within body 12 for diagnosis or treatment. For example, system 10 may be used to determine the position of an electrophysiological (EP) mapping catheter or an intradcardiac echocardiography (ICE) catheter. Further, it should be understood that the system may be used to determine the position of medical devices used in the diagnosis or treatment of portions of body 12 other than the tissue 16. System 10 may include a remote control guidance system (RCGS) 18 for catheter 14, an electric field based positioning system 20, a magnetic field based positioning system 22, a display 24 and an electronic control unit (ECU) 26.

Figure 2:
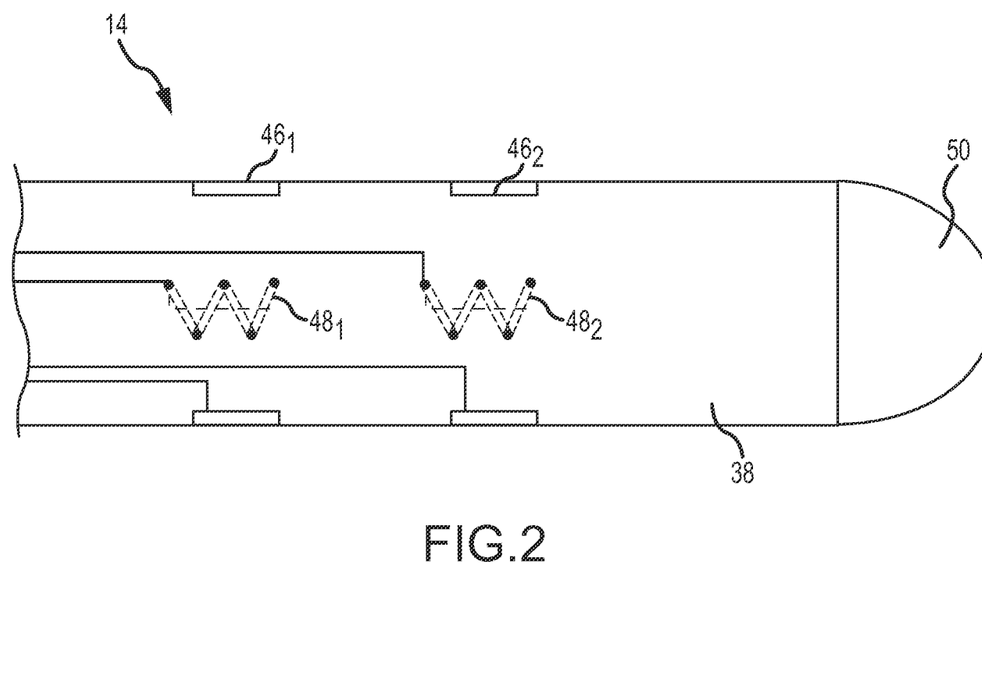
FIG. 2 is a view of a portion of an exemplary medical device for use in the system of FIG. 1.

Catheter 14 is provided for examination, diagnosis and treatment of internal body tissues such as cardiac tissue 16. In accordance with one embodiment, catheter 14 comprises an ablation catheter and, more particularly, an irrigated radio-frequency (RF) ablation catheter. It should again be understood, however, that catheter 14 is provided for illustration only and that system 10 could be adapted for use with a variety of catheters including, for example, electrophysiology mapping catheters and intracardiac echocardiograph (ICE) catheters, as well as for use with other types of ablation catheters including those providing different types of ablation energy (e.g., cryoablation, ultrasound, etc.). Catheter 14 may be connected to a fluid source 28 having a biocompatible fluid such as saline through a pump 30 (which may comprise, for example, a fixed rate roller pump or variable volume syringe pump with a gravity feed supply from fluid source 28 as shown) for irrigation. Catheter 14 is also electrically connected to an ablation generator 32 for delivery of RF energy. Catheter 14 may include a cable connector or interface 34, a handle 36, a shaft 38 having a proximal end 40 and a distal end 42 (as used herein, "proximal" refers to a direction toward the end of the catheter near the physician, and "distal" refers to a direction away from the physician and (generally) inside the body of a patient) and one or more electrodes 44. Referring to FIG. 2, in accordance with one aspect of the present teachings, catheter 14 further includes multiples types of position sensors including, in the illustrated embodiment, one or more electrical position sensors $46_1, 46_2 \ldots 46_K$ and one or more magnetic position sensors $48_1, 48_2 \ldots 48_J$ for a purposed described hereinbelow. Catheter 14 may also include other conventional components not illustrated herein such as a temperature sensor, additional electrodes, and corresponding conductors or leads.

Connector 34 provides mechanical, fluid and electrical connection(s) for conduits or cables extending from RCGS 18, pump 30, and ablation generator 32. Connector 34 is conventional in the art and is disposed at a proximal end of catheter 14.

Handle 36 provides a location for the physician to hold catheter 14 and may further provides means for steering or guiding shaft 38 within body 12. For example, handle 36 may include means to change the length of a guidewire (either manually or under the control of RCGS 18) extending through catheter 14 to distal end 42 of shaft 38 to steer distal end 42 and, thus, shaft 38. Handle 36 is also conventional in the art and it will be understood that the construction of handle 36 may vary.

Shaft 38 is an elongated, flexible member configured for movement within body 12. Shaft 38 supports electrodes 44, position sensors $46_1, 46_2 \ldots 46_K, 48_1, 48_2 \ldots 48_J$, associated conductors, and possibly additional electronics used for signal processing or conditioning. Shaft 38 may also permit transport, delivery, and/or removal of fluids (including irrigation fluids and bodily fluids), medicines, and/or surgical tools or instruments. Shaft 38 may be made from conventional materials such as polyurethane and defines one or more lumens configured to house and/or transport electrical conductors, fluids, or surgical tools. Shaft 38 may be introduced into a blood vessel or other structure within body 12 through a conventional introducer sheath. Shaft 38 may then be steered or guided through body 12 to a desired location such as tissue 16 using guide wires or pullwires or other means known in the art including remote control guidance systems.

Electrodes 44 may be provided for a variety of diagnostic and therapeutic purposes including, for example, electro-physiological studies, catheter identification and location, pacing, and cardiac mapping and ablation. Referring to FIG. 2, in the illustrated embodiment, catheter 14 includes an ablation tip electrode 50 at distal end 42 of shaft 38. It should be understood, however, that the number, orientation, and purpose of electrodes 44 may vary.

Electrical position sensors $46_1, 46_2 \ldots 46_K$ are provided for use in determining the position of catheter 14 within body 12. Sensors $46_1, 46_2 \ldots 46_K$ are conventional in the art. In the illustrated embodiment, sensors $46_1, 46_2 \ldots 46_K$ comprise electrodes and, in particular, conventional ring electrodes located proximal to the distal end 42 of catheter shaft 38 and tip electrode 50. As sensors $46_1, 46_2 \ldots 46_K$ move within body 14, and within the electric field generated by system 20, the voltage readings from sensors $46_1, 46_2 \ldots 46_K$ change thereby indicating the location of sensors $46_1, 46_2 \ldots 46_K$ within the electric field and with a coordinate system 52 established by system 20. Sensors $46_1, 46_2 \ldots 46_K$ communicate position signals to ECU 26 through a conventional interface (not shown).

Magnetic position sensors $48_1, 48_2 \ldots 48_J$ are also provided for use in determining the position of catheter 14 within body 12. In the illustrated embodiment, sensors $48_1, 48_2 \ldots 48_J$ are coils. As sensors $48_1, 48_2 \ldots 48_J$ move within body 14, and within the magnetic field generated by system 22, the current output of each sensor $48_1, 48_2 \ldots 48_J$ changes thereby indicating the location of sensors $48_1, 48_2 \ldots 48_J$ within the magnetic field and within a coordinate system 54 established by system 22. Sensors $48_1, 48_2 \ldots 48_J$ may be wound about catheter 14 at or near distal end 42 and may be embedded within the walls of catheter 14 such that sensors $48_1, 48_2 \ldots 48_J$ are insulated. Alternatively, sensors $48_1, 48_2 \ldots 48_J$ could be embedded further within catheter 14 as shown in FIG. 2, or could be placed at other locations within the catheter 14. Sensors $48_1, 48_2 \ldots 48_J$ may also have appropriate insulation and/or shielding (e.g., a conductive foil or wire mesh) to cancel potential interferences from other devices near body 12. It should be understood that sensors $48_1, 48_2 \ldots 48_J$ may take forms other than the form illustrated in FIG. 2. Sensors $48_1, 48_2 \ldots 48_J$ may, for example, comprise any conventional position sensors for detecting changes in magnetic fields including Hall effect sensors, magnetoresistive sensors and sensors made from magnetoresistive materials and piezoelectric materials and the like. Sensors $48_1, 48_2 \ldots 48_J$ communicate position signals to ECU 26 through a conventional interface (not shown). In accordance with one aspect of the present teachings, each of magnetic position sensors $48_1, 48_2 \ldots 48_J$ is disposed proximate to a corresponding electrical position sensor $46_1, 46_2 \ldots 46_K$ such that the detected position of one of sensors 46, 48 may be indicative of the position of the other corresponding sensor 46, 48. The magnetic position sensors $48_1, 48_2 \ldots 48_J$ may, for example be located from about 1.0 to about 3.0 millimeters from a corresponding electrical position sensor $46_1, 46_2 \ldots 46_K$ and may be centered between two electrical position sensors $46_1, 46_2 \ldots 46_K$ which may be spaced about 2.0 to 6.0 millimeters apart.

RCGS 18 is provided to manipulate catheter 14. In particular, RCGS 18 permits control of translation, distal bending, and rotation of catheter 18 and any surrounding sheath. RCGS 18 therefore provides the user with a type of control similar to that provided by conventional manually-operated systems, but allows for repeatable, precise, and dynamic movements. A physician may identify target locations (potentially forming a path) on an image of tissue 16. RCGS 18 relates these digitally selected points to positions within the patient's actual/physical anatomy, and may thereafter generates commands to control the movement of catheter 14 to the defined positions where the physician or the RCGS 18 can perform the desired diagnostic of therapeutic function. A more complete description of various elements of an exemplary RCGS may be found in the following published patent applications that are incorporated herein by reference: U.S. Publication No. 2009/0247942; U.S. Publication No. 2009/0247944; U.S. Publication No. 2009/0247993; U.S. Publication No. 2009/0248042; U.S. Publication No. 2010/0256558; U.S. Publication No. 2011/0015569 and PCT Publication No. WO 2009/120982.

System 20 is provided to determine the position and orientation of catheter 14 and similar devices within body 12. System 20 may comprise the system made available under the trademark "ENSITE NAVX" by St. Jude Medical, Inc. and described, for example, in U.S. Pat. No. 7,263,397, the entire disclosure of which is incorporated herein by reference. The system is based on the principle that when low amplitude electrical signals are passed through the thorax, body 12 acts as a voltage divider (or potentiometer or rheostat) such that the electrical potential or field strength measured at an electrode such as one of position sensors $46_1, 46_2 \ldots 46_K$ on catheter 14 may be used to determine the position of the electrode, and therefore catheter 14, relative to a pair of external patch electrodes using Ohm's law and the relative location of a reference electrode (e.g. in the coronary sinus). In one configuration, the system includes three pairs of patch electrodes 56 that are placed on opposed surfaces of body 12 (e.g., chest and back, left and right sides of the thorax, and neck and leg) and form generally orthogonal x, y, and z axes as well as a reference electrode/patch (not shown) that is typically placed near the stomach and provides a reference value and acts as the origin of the coordinate system 52 for the navigation system. Sinusoidal currents are driven through each pair of patch electrodes 56 and voltage measurements for one or more position sensors $46_1, 46_2 \ldots 46_K$ associated with catheter 14 are obtained. The measured voltages are a function of the distance of the position sensors $46_1, 46_2 \ldots 46_K$ from the patch electrodes 56. The measured voltages are compared to the potential at the reference electrode and a position of the position sensors $46_1, 46_2 \ldots 46_K$ within the coordinate system 52 of the navigation system is determined. In accordance with this exemplary system, system 18 may include patch electrodes 56 (namely $56_{X1}, 56_{X2}, 56_{Y1}, 56_{Y2}, 56_{Z1}, 56_{Z2}$) a switch 58, and a signal generator 60.

Patch electrodes 56 are provided to generate electrical signals used in determining the position of catheter 14 within three-dimensional coordinate system 52 of system 20. Electrodes 56 may also be used to generate EP data regarding tissue 16. Electrodes 56 are placed orthogonally on the surface of body 12 and are used to create axes specific electric fields within body 12. Electrodes $56_{X1}, 56_{X2}$ may be placed along a first (x) axis. Similarly, electrodes $56_{Y1}, 56_{Y2}$ may be placed along a second (y) axis, and electrodes $56_{Z1}, 56_{Z2}$ may be placed along a third (z) axis. Each of the electrodes 56 may be coupled to multiplex switch 58. ECU 26 is configured through appropriate software to provide control signals to switch 58 and thereby sequentially couple pairs of electrodes 56 to signal generator 60. Excitation of each pair of electrodes 56 generates an electromagnetic field within body 14 and within an area of interest such as the heart. Voltage levels at non-excited electrodes 56 may be filtered and converted and provided to ECU 26 for use as reference values.

System 22 is also provided to determine the position and orientation of catheter 14 and similar devices within body 12. System 22 comprises a system that employs magnetic fields to detect the position of catheter 14 within body 12 such as the system made available under the trademark "MEIGUIDE" by St. Jude Medical, Inc. and generally shown and described in, for example, U.S. Pat. No. 7,386,339, the entire disclosure of which is incorporated herein by reference. In such a system, a magnetic field generator 62 may be employed having three orthogonally arranged coils, arranged to create a magnetic field within body 12 and to control the strength, orientation, and frequency of the field. The magnetic field generator 62 may be located above or below the patient (e.g., under a patient table) or in another appropriate location. Magnetic fields are generated by the coils and current or voltage measurements for one or more position sensors $48_1, 48_2 \ldots 48_J$ associated with catheter 14 are obtained. The measured currents or voltages are proportional to the distance of the sensors $48_1, 48_2 \ldots 48_J$ from the coils thereby allowing a position of the sensors $48_1, 48_2 \ldots 48_J$ within a coordinate system 54 of system 22.

Display 24 is provided to convey information to a physician to assist in diagnosis and treatment. Display 24 may comprise one or more conventional computer monitors or other display devices. Display 24 may present a graphical user interface (GUI) to the physician. The GUI may include a variety of information including, for example, an image of the geometry of tissue 16, electrophysiology data associated with the tissue 16, graphs illustrating voltage levels over time for various electrodes 44, and images of catheter 14 and other medical devices and related information indicative of the position of catheter 14 and other devices relative to the tissue 16.

ECU 26 provides a means for controlling the operation of various components of system 10 including catheter 14, RCGS 18, ablation generator 32, switch 58 of system 20, and magnetic generator 62 of system 22. ECU 26 may also provide a means for determining the geometry of tissue 16, electrophysiology characteristics of tissue 16 and the position and orientation of catheter 14 relative to tissue 16 and body 12. ECU 26 also provides a means for generating display signals used to control display 24. ECU 26 may comprise one or more programmable microprocessors or microcontrollers or may comprise one or more application specific integrated circuits (ASICs). ECU 26 may include a central processing unit (CPU) and an input/output (I/O) interface through which ECU 26 may receive a plurality of input signals including signals generated by RCGS 18, ablation generator 32, electrodes 44 and position sensors $46_1, 46_2 \ldots 46_K, 48_1, 48_2 \ldots 48_J$ on catheter 14, and patch electrodes 56 of system 20, and generate a plurality of output signals including those used to control and/or provide data to catheter 14, RCGS 18, display 24, ablation generator 32, switch 58 of system 20, and generator 62 of system 22.

In accordance with the present teachings, ECU 26 may be configured with programming instructions from a computer program (i.e., software) to implement a method for determining a position of catheter 14 within body 12. The program may be stored in a computer storage medium such as a memory (not shown) that is internal to ECU 26 or external to ECU 26 and may be pre-installed in the memory or obtained from a computer storage medium external to device 10 including from various types of portable media (e.g., compact discs, flash drives, etc.) or file servers or other computing devices accessible through a telecommunications network.

Figure 3:
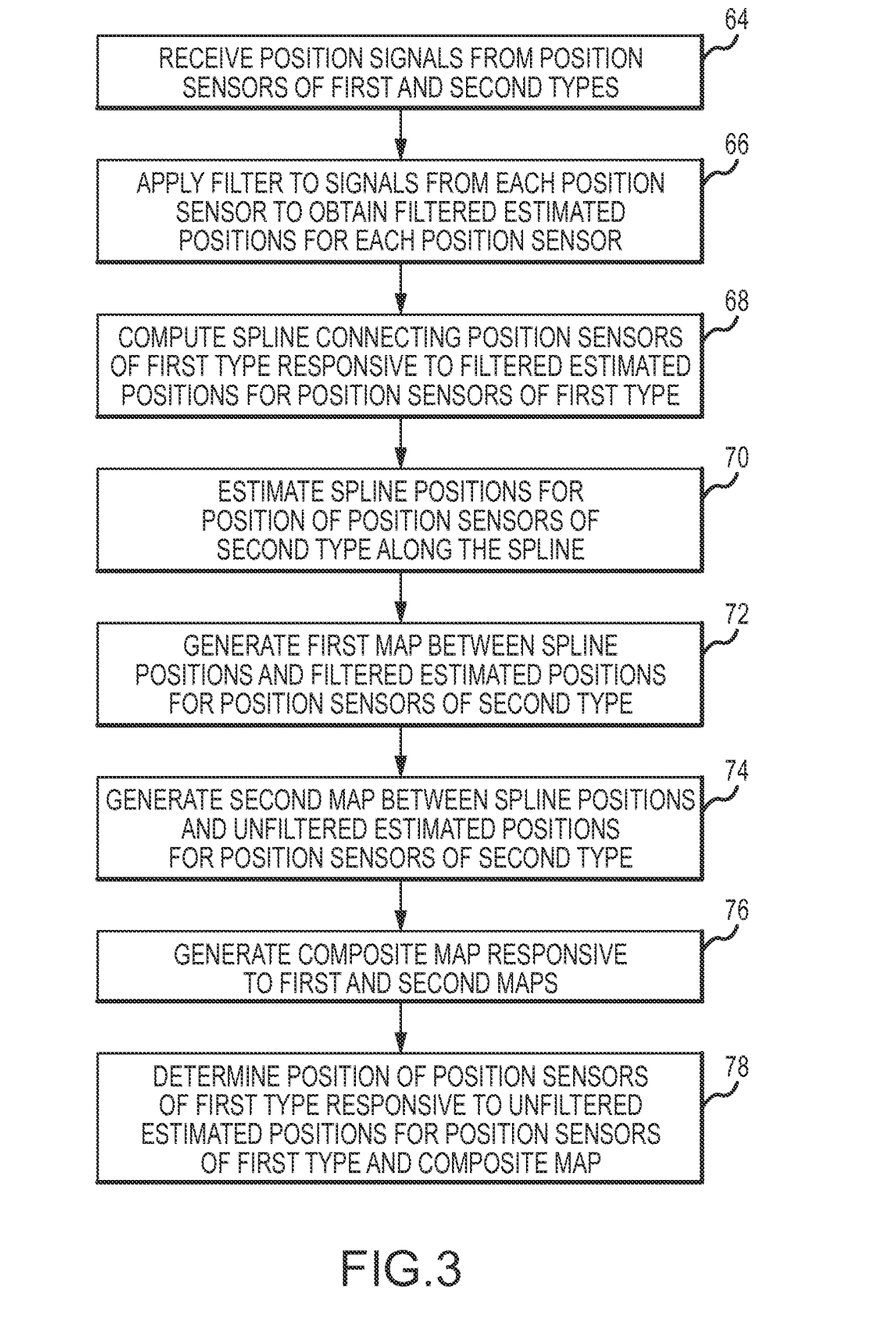
FIG. 3 is a flow-chart diagram illustrating one embodiment of a method for determining a position of a medical device within a body in accordance with the present teachings.

Referring to FIG. 3, an exemplary method for determining a position of a medical device within a body may begin with the step 64 of receiving position signals from plurality of position sensors of a first type disposed on catheter 14 and at least one position sensor of a second type disposed on catheter 14. In the embodiment described hereinbelow, ECU 26 receives signals from a plurality of electrical position sensors $46_1, 46_2 \ldots 46_K$ and at least one position sensor $48_1$ with the objective of using positional information from sensor $48_1$—which generates signals with very little if any noise—to improve the accuracy of position information from sensors $46_1, 46_2 \ldots 46_K$ which are subject to relatively high levels of noise. It should be understood, however, that other embodiments in accordance with the disclosed teachings could be used with a variety of different types of sensors to leverage a beneficial characteristic of one type of sensor in interpreting information generated by another type of sensor.

The method may continue with the step 66 of applying a filter (e.g., a linear time invariant digital filter) to each of the position signals received from sensors $46_1, 46_2 \ldots 46_K, 48_1$ to obtain filtered estimated positions for each of position sensors $46_1, 46_2 \ldots 46_K, 48_1$:

$$x[n] = -\sum_{k=1}^{N} a[k]x[n-k] + \sum_{k=0}^{M} b[k]y[n-k];$$

$$x_e = f(y_e);$$

$$x_m = f(y_m);$$

$$x_e[n] = f(y_e)[n];$$

and, $$x_m[n] = f(y_m)[n]$$

where $f(y_e)$ is a function that performs filtering on the series of the observed values $y_e$ for the position of electrical position sensor 46 to produce the series filtered values $x_e$, $f(y_m)$ is a function that performs filtering on the series of the observed values $y_m$ for the position of magnetic position sensor 48 to produce the series of filtered values $x_m$, the notation $x[n]=f(y)[n]$ indicates that the filtered value at time n has been selected from the series, $x_e[n]$ is the estimated filtered position of an electrical position sensor 46 at time n, and $x_m[n]$ is the estimated filtered position of a magnetic position sensor 48 at time n. The filter may comprise any of a variety of filters used in removing signal noise including a linear filter such as an infinite impulse response filter or a finite impulse response filter or an adaptive filter such as a Kalman filter. In one embodiment, a two pole inverse Chebychev lowpass filter cascaded with a two pole Butterworth lowpass filter is used. It should be understood, however, that a variety of filters may be employed and, in some embodiments, the same filter is applied to signals from both types of position sensors.

The method may continue with the step 68 of computing a spline connecting position sensors $46_1, 46_2 \ldots 46_K$ responsive to the filtered estimated positions for sensors $46_1, 46_2 \ldots 46_K$. Multiple types of splines may be used to provide an interpolation between position sensors $46_1, 46_2 \ldots 46_K$. The splines may comprise, for example, b-splines, cubic splines or thin-plate splines. In addition to the filtered estimated positions for sensors $46_1$, $46_2$ ... $46_K$, other constraints could be applied in determining the spline such as a constraint based on the material of the catheter shaft 38 in order to limit oscillations of catheter 14 that are not physically possible.

The method may continue with the step 70 of estimating a spline position $g_m(\vec{y}_e)[n]$ for position sensor $48_1$ along the spline, determined from a plurality of filtered position sensors $46_1$ to $46_K$. As discussed hereinabove, sensors $46_1$, $46_2$ ... $46_K$ and $48_1$, $48_2$ ... $48_J$ have a known positional relationship relative to one another. Therefore, using the known position of sensors $46_1$, $46_2$ ... $46_K$ along the spline, the position of any of sensors $48_1$, $48_2$ ... $48_J$ along the spline can be estimated.

The method may continue with the steps 72, 74 of generating a map between the spline position $g_m(\vec{y}_e)[n]$ of sensor $48_1$ and the filtered estimated position $f(y_m)$ of sensor $48_1$ achieved in step 66 and a map between the spline position $g_m(\vec{y}_e)[n]$ of sensor $48_1$ and the unfiltered estimated position $y_m$ of sensor $48_1$. In an embodiment in which only changes in the relative location—and not orientation—of sensor $48_1$ are used in determining the position of sensors $46_1$, $46_2$ ... $46_K$, and therefore catheter 14, the maps may comprise vector offsets $t_f$ and $t_u$ between the spline position $g_m(\vec{y}_e)[n]$ of sensor $48_1$ and the filtered estimated position $f(y_m)$ and unfiltered estimated position $y_m$ of sensor $48_1$, respectively:

$$t_f = f(y_m) - g(\vec{y}_e)$$

$$t_u = y_m - g(\vec{y}_e)$$

In other embodiments of the invention, changes in both the relative location and orientation of sensor $48_1$ are used in determining the position of sensors $46_1$, $46_2$ ... $46_K$, and therefore catheter 14. In these embodiments, the maps may comprise transformation matrices $Tr_f$ and $Tr_u$ between the spline position $g_m(\vec{y}_e)[n]$ of sensor $48_1$ and the filtered estimated position $f(y_m)$ and unfiltered estimated position $y_m$ of sensor $48_1$, respectively. In still other embodiments of the invention, a plurality of magnetic position sensors $48_1$, $48_2$ ... $48_J$ may be used as fiducial points to determine the positions of sensors $46_1$, $46_2$ ... $46_K$, and therefore catheter 14. In these embodiments, the maps may comprise transformation functions between the spline positions $g_m(\vec{y}_e)[n]$ of sensors $48_1$, $48_2$ ... $48_J$ and the filtered estimated position $f(y_m)$ and unfiltered estimated position $y_m$ of sensors $48_1$, $48_2$ ... $48_J$, respectively. In accordance with one embodiment, the transformation functions may comprise the inverse thin spline transformation functions $TPS_f^{-1}(\ )$ between the spline positions $g_m(\vec{y}_e)[n]$ of sensors $48_1$, $48_2$ ... $48_J$ and the filtered estimated position $f(y_m)$ and the thin plate spline function $TPS_u(\ )$ between the spline positions $g_m(\vec{y}_e)[n]$ of sensor $48_1$, $48_2$ ... $48_J$ and the unfiltered estimated position $y_m$ of sensors $48_1$, $48_2$ ... $48_J$.

The method may continue with the step 76 of generating a composite map responsive to the maps between the spline position $g_m(\vec{y}_e)[n]$ of the position sensor $48_1$ (or sensors $48_1$, $48_2$ ... $48_J$) and the filtered estimated position $f(y_m)$ and unfiltered estimated position $y_m$ of sensor $48_1$ (or sensors $48_1$, $48_2$ ... $48_J$). In the embodiment where the maps comprise vector offsets, the composite map may be generated by subtraction of one map from the other:

$$t = t_u - t_f$$

In the embodiment where the maps comprise transformation matrices, the composite map may be generated by multiplication of the maps:

$$Tr = Tr_f^{-1} * Tr_u$$

In the embodiment where the maps comprise transformation functions, the composite map may be generated by successive application of the functions to the filtered estimated position $f(y_e)$ of the electrical position sensors $46_1$, $46_2$ ... $46_K$.

The method may continue with the step 78 of determining an actual position for one or more of position sensors $46_1$, $46_2$ ... $46_K$ responsive to the composite map and the filtered estimated position for the respective position sensor $46_1$, $46_2$ ... $46_K$. In the embodiment where the composite map is derived from maps comprising vector offsets, the actual positions $f'(y_e)$ of sensors $46_1$, $46_2$ ... $46_K$ may be determined as follows:

$$f'(y_e) = f(y_e) + t$$

In embodiments where the composite map is derived from maps comprising transformation matrices, the actual positions $f'(y_e)$ of sensors $46_1$, $46_2$ ... $46_K$ may be determined as follows:

$$f'(y_e) = Tr * f(y_e)$$

In embodiments where the composite map is derived from maps comprising transformation functions, the actual positions $f'(y_e)$ of sensors $46_1$, $46_2$ ... $46_K$ may be determined as follows:

$$f'(y_e) = TPS_f^{-1}(TPS_u(f(y_e)))$$

A system 10 and method for determining a position of a medical device such as a catheter 14 within a body 12 in accordance with the present teachings enables efficient and accurate position detection by making use of the beneficial characteristics of multiple types of position sensors. In the illustrated embodiment, for example, position information from magnetic position sensors $48_1$, $48_2$ ... $48_J$ whose signals have very little noise is used to adjust position information from electrical position sensors $46_1$, $46_2$ ... $46_K$ which suffer from higher levels of noise, but are less expensive and easier to implement in large numbers on catheter 14.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for determining a position of a medical device within a body, comprising:
an electronic control unit configured to:
receive a position signal from each of a plurality of position sensors of a first type disposed on the medical device and from at least one position sensor of a second type disposed on the medical device;
apply a filter to each of said position signals to obtain filtered estimated positions for each of said plurality of position sensors of said first type and said at least one position sensor of said second type;
compute a spline connecting said plurality of position sensors of said first type responsive to said filtered estimated positions for said plurality of positions sensors of said first type;
estimate a spline position for said at least one position sensor of said second type along said spline;
generate a first map between said spline position and said filtered estimated position of said at least one position sensor of said second type;
generate a second map between said spline position and an unfiltered estimated position of said at least one position sensor of said second type;
generate a composite map using said first and second maps;
determine an actual position for one of said plurality of position sensors of said first type using said composite map and said filtered estimated position for said one of said plurality of position sensors of said first type; and
a display communicatively coupled to the electronic control unit and configured and arranged to display the composite map overlaid with the actual position of said one of said plurality of position sensors of said first type.

2. The system of claim 1 wherein said first type of position sensor comprises an electrical position sensor.

3. The system of claim 2 wherein said second type of position sensor comprises a magnetic position sensor.

4. The system of claim 1 wherein said second type of position sensor comprises a magnetic position sensor.

5. The system of claim 1 wherein said first and second maps comprise vector offsets between said spline position and corresponding said filtered estimated position and said unfiltered estimated position of said at least one position sensor of said second type.

6. The system of claim 1 wherein said first and second maps comprise transformation matrices between said spline position and corresponding said filtered estimated position and said unfiltered estimated position of said at least one position sensor of said second type.

7. The system of claim 1 wherein said at least one position sensor of said second type comprises a plurality of position sensors of said second type and said first and second maps comprise transformation functions between said spline positions for said plurality of position sensors of said second type and corresponding ones of said filtered estimated positions and said unfiltered estimated positions of said plurality of position sensors of said second type.

8. The system of claim 7 wherein said transformation functions comprise thin plate spline transformation functions.

9. The system of claim 1, wherein the electronic control unit is further configured to generate the composite map by subtracting, adding, multiplying, or dividing the first and second maps, respectively.

10. A method for determining a position of a medical device within a body, comprising:
receiving a position signal from each of a plurality of position sensors of a first type disposed on the medical device and from at least one position sensor of a second type disposed on the medical device;
applying a filter to each of said position signals to obtain filtered estimated positions for each of said plurality of position sensors of said first type and said at least one position sensor of said second type;
computing a spline connecting said plurality of position sensors of said first type responsive to said filtered estimated positions for said plurality of positions sensors of said first type;
estimating a spline position for said at least one position sensor of said second type along said spline;
generating a first map between said spline position and said filtered estimated position of said at least one position sensor of said second type;
generating a second map between said spline position and an unfiltered estimated position of said at least one position sensor of said second type;
generating a composite map using said first and second maps;
determining an actual position for one of said plurality of position sensors of said first type using said composite map and said filtered estimated position for said one position sensor of said first type; and
a display communicatively coupled to the electronic control unit and configured and arranged to display the composite map overlaid with the actual position of said one of said plurality of position sensors of said first type.

11. The method of claim 10 wherein said first type of position sensor comprises an electrical position sensor.

12. The method of claim 11 wherein said second type of position sensor comprises a magnetic position sensor.

13. The method of claim 10 wherein said second type of position sensor comprises a magnetic position sensor.

14. The method of claim 10 wherein said first and second maps comprise vector offsets between said spline position and corresponding said filtered estimated position and said unfiltered estimated position of said at least one position sensor of said second type.

15. The method of claim 10 wherein said first and second maps comprise transformation matrices between said spline position and corresponding said filtered estimated position and said unfiltered estimated position of said at least one position sensor of said second type.

16. The method of claim 10 wherein said at least one position sensor of said second type comprises a plurality of position sensors of said second type and said first and second maps comprise transformation functions between said spline positions for said plurality of position sensors of said second type and corresponding ones of said filtered estimated positions and said unfiltered estimated positions of said plurality of position sensors of said second type.

17. The method of claim 16 wherein said transformation functions comprise thin plate spline transformation functions.

18. The method of claim 10, wherein generating the composite map comprises subtracting, adding, multiplying, or dividing the first and second maps, respectively.

* * * * *